(12) United States Patent
Niu et al.

(10) Patent No.: US 7,741,534 B2
(45) Date of Patent: Jun. 22, 2010

(54) CYTOKININ OXIDASE PROMOTER FROM MAIZE

(75) Inventors: Xiaomu Niu, Johnston, IA (US); Haiyin Wang, Johnston, IA (US); Dwight T Tomes, Van Meter, IA (US); Sabine Hantke, Cologne (DE); Norbert Brugiere, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 253 days.

(21) Appl. No.: 12/051,893

(22) Filed: Mar. 20, 2008

(65) Prior Publication Data

US 2008/0172760 A1 Jul. 17, 2008

Related U.S. Application Data

(60) Division of application No. 11/074,144, filed on Mar. 7, 2005, now Pat. No. 7,371,925, which is a continuation-in-part of application No. 10/109,488, filed on Mar. 28, 2002, now Pat. No. 6,921,815.

(60) Provisional application No. 60/279,805, filed on Mar. 29, 2001.

(51) Int. Cl.
 *C12N 15/82* (2006.01)
(52) U.S. Cl. ............... 800/285; 800/287; 536/24.1; 435/468
(58) Field of Classification Search .............. None
See application file for complete search history.

(56) References Cited

U.S. PATENT DOCUMENTS 6,229,066 B1   5/2001   Morris
7,230,168 B2 *  6/2007   Huang et al. ............ 800/303

FOREIGN PATENT DOCUMENTS

WO   9906571  A1   2/1999
WO   WO 99/06571   * 11/1999

OTHER PUBLICATIONS

Knoester, et al.; "Ethylene-insensitive tobacco lacks nonhost resistance against soil-borne fungi": Proc National Acad Sci USA (1998) 95:1933-1937.
Matsuoka, et al.; "Tissue-specific light-regulated expression directed by the promoter of a C4 gene, maize pyruvate, orthophosphate dikinase, in a C3 plant, rice"; Prac Natl Acad Sci USA (1993) 90:9586-9590.
Sayanova, et al.; "Expression of a borage desaturase cDNA containing an N-terminal cytochrome b5 domain results in the accumulation of high levels of a delta-6-desaturated fatty acids in transgenic tobacco"; Proc Natl Acad Sci USA (1997) 94:4211-4216.
Umeda, et al.; "A cyclin-dependent kinase-activating kinase regulated differentiation of root initial cells in Arabidopsis"; PNAS (2000) 97(24):13396-13400.
Yang, et al.; "Maize sucrose synthase-1 promoter direct phloem cell-specific expression of Gus gene in transgenic tobacco plants"; Proc Natl Acad Sci USA (1990) 87:4144-4148.
Houba-Herin, et al.; "Cytokinin oxidase from Zea mays: purification, cDNA cloning and expression in moss protoplasts"; The Plant Journal (1999) 17(6):615-626.
Morris, et al.; "Isolation of a Gene Encoding Glycosylated Cytokinin Oxidase from Maize"; Biochemical and Biophysical Communications (1999) 255:328-333.
NCBI Database Accession No. Y18377 (1999).
NCBI Database Accession No. AF0044603 (1999).
Joshi, et al.; "Pearl Millet Cysteine Protease Inhibitor"; Eur J Biochem (1999) 265:556-563.

* cited by examiner

*Primary Examiner*—Russell Kallis

(57) ABSTRACT

The present invention provides compositions and methods for regulating expression of nucleotide sequences in a plant. Compositions may comprise a novel nucleic acid sequence for a promoter with tissue specificity and/or cytokinin inducibility. A method for expressing a heterologous nucleotide sequence in a plant using the promoter sequence is also provided. The method comprises transforming a plant cell to contain a heterologous nucleotide sequence operably linked to the promoter of the present invention and regenerating a stably transformed plant from the transformed plant cell. Other methods provide for downregulation of cytokinin oxidase in a plant.

2 Claims, 1 Drawing Sheet

CYTOKININ OXIDASE PROMOTER FROM MAIZE

CROSS-REFERENCE TO RELATED APPLICATIONS

This application is a divisional application of U.S. patent application Ser. No. 11/074,144 filed Mar. 7, 2005 now U.S. Pat. No. 7,371,925 which is a continuation-in-part of U.S. patent application Ser. No. 10/109,488, filed Mar. 28, 2002 now U.S. Pat. No. 6,921,815, which claims the benefit of and incorporates by reference U.S. Provisional patent application No. 60/279,805, filed Mar. 29, 2001.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably-linked promoter that is functional within the plant host. Choice of the promoter sequence will determine when and where within the plant the heterologous DNA sequence is expressed. Where continuous expression is desired throughout the cells of a plant, constitutive promoters are utilized. In contrast, where gene expression in response to a stimulus is desired, inducible promoters are the regulatory elements of choice. Where expression in specific tissues or organs is desired, tissue-preferred promoters are used. That is, these promoters can drive expression in specific tissues or organs. Additional regulatory sequences upstream and/or downstream from the core promoter sequence can be included in expression cassettes of transformation vectors to bring about varying levels of expression of heterologous nucleotide sequences in a transgenic plant. See, for example, U.S. Pat. No. 5,850,018.

Regulatory sequences may also be useful in controlling temporal and/or spatial expression of endogenous DNA. For example, specialized tissues are involved in fertilization and seed development. Identification of promoters which are active in these seed tissues is of interest.

In grain crops of agronomic importance, seed formation is the ultimate goal of plant development. Seeds are harvested for use in food, feed, and industrial products. The quantities and proportions of protein, oil, and starch components in those seeds determine their utility and value.

The timing of seed development is critical. Environmental conditions at any point prior to fertilization through seed maturation may affect the quality and quantity of seed produced. In particular, the first 10 to 12 days after pollination (the lag phase) are critical in maize seed development. Several developmental events during the lag phase are important determinants of the fate of subsequent seed growth and development. (Cheikh, et al., (1994) *Plant Physiology* 106:45-51) Therefore, a means to influence plant development, particularly in response to stress during this phase of growth, is of interest. Identification of a promoter sequence active in tissues of developing seeds exposed to abiotic stresses would be useful.

Specialized plant tissues are central to seed development. Following fertilization, developing seeds become sinks for carbon translocated via the phloem from sites of photosynthesis. However, developing cereal seeds have no direct vascular connections with the plant; instead, a short-distance transport mechanism operates to move the assimilates from the vascular tissues to the endosperm and embryo. For example, in maize, photosynthate enters the seed via the pedicel; in wheat, via the nucellar projection and the aleurone layer. It is possible that this short-distance assimilate pathway between the phloem and the endosperm can operate to regulate the rate of sucrose transport into the grain. (Bewley and Black. *Seeds: Physiology of Development and Germination*. N.Y., Plenum Press, 1985. pp. 38-39). Therefore, a promoter active in gene expression within these specialized tissues, such as the pedicel, may have significant effects on grain development.

During rapid seed growth, sucrose is unloaded passively from the phloem into the apoplast of the pedicel parenchyma and inverted to hexose sugars by a cell-wall-bound acid invertase. The hydrolysis of sucrose in the apoplast maintains a favorable gradient for continued unloading from the phloem and provides hexoses that are taken up by the basal endosperm cells. It has been shown that seeds induced to abort, in vitro, have only low levels of invertase activity in the pedicel. (Hanft, et al., (1986) *Plant Physiol.* 81:503-510)

Water stress to the plant around anthesis often results in seed abortion or restricted development. Studies suggest that sucrose continues to unload from the phloem at low ovary water potential, but it accumulates in the symplasm and apoplasm of the pedicel because of low invertase activity. (Zinselmeier, et al., (1995) *Plant Physiol.* 107:385-391) This conclusion is supported by the findings of Miller and Chourey (*Plant Cell* 4:297-305 (1992)), who showed that developmental failure of miniature-1 seeds of maize was linked to lack of invertase activity in the pedicel tissue during the early stages of seed development.

Other specialized plant tissues are also closely involved in the critical processes of fertilization and seed development. For example, in maize, the carpels, which make up the ovary wall, become the pericarp, a tough, protective outer seed covering. The scutellum, along with the endosperm, is involved in translocation of assimilates to the developing embryo. The aleurone, the surface layer of endosperm cells, develops to serve as a source of enzymes necessary in germination. (Kiesselbach, *The Structure and Reproduction of Corn*. N.Y., Cold Spring Harbor Press, 1999)

To achieve yield stability in high-density plantings, under drought conditions, or in other adverse environments, modification of carbohydrate metabolism during early ear and kernel development may be desirable. Effective control of genes involved in carbohydrate metabolism is dependent on identification and use of a promoter with high levels of tissue and temporal specificity. Specifically desired expression targets include pedicel, pericarp, and nucellus tissue during a period 14 days before pollination to 14 days after pollination.

In light of the important contributions of these specialized seed tissues to proper grain development, identification of a promoter sequence affecting gene expression in these tissues would be useful. Further, it would be desirable to identify a promoter sequence active in these specific tissues at appropriate, critical times. Even more desirable would be the identification of a promoter sequence active in these specific tissues at appropriate, critical times, which is not negatively affected by environmental stress to the plant.

The maize Glb1 gene encodes globulin-1, a major embryo storage protein. (Kriz, et al. (1986) *Plant Physiol.* 82:1069-1075) Glb1 is expressed in the developing maize seed during embryo development. (Belanger, et al., (1989) *Plant Physiol.* 91:636-643) The promoter region of Glb1 has been identified, cloned, and introduced into tobacco plants by *Agrobacterium*-mediated transformation. (Liu, et al., (1996) *Plant Cell*

Reports 16:158-162) The transformed plants demonstrate that the Glb1 promoter has desirable temporal and tissue specificity. However, the Glb1 promoter is positively regulated by abscisic acid (ABA). (Kriz, et al. (1990) *Plant Physiol.* 92:538-542; Paiva, et al., (1994) *Planta* 192:332-339) Levels of the plant hormone ABA are known to fluctuate under conditions of cold or desiccation. (Himmelbach, et al. (1998) *Phil. Trans. R. Soc. Lond.* 353:1439-1444) Thus, the activity of the Glb1 promoter can be differentially affected by environmental stress.

A maize cytokinin oxidase gene has been isolated and sequenced (GenBank entry AF044603). Cytokinin oxidase inactivates cytokinins, members of a class of plant hormones important in the control of cell division and in regulation of plant growth and structure. Elevated cytokinin levels are associated with the development of seeds in higher plants; exogenous cytokinin application has been shown to directly correlate with increased kernel yield in maize. Thus, control of the level of cytokinin oxidase has been suggested as a tool in improving grain yield. Manipulation of cytokinin oxidase activity has also been proposed as a means to achieve greater disease resistance or other improved plant characteristics. (See, WO 99/06571, herein incorporated by reference.)

However, a novel and heretofore undescribed utility of the isolated cytokinin oxidase gene is as a source of a promoter sequence with spatial and temporal specificity and which may be induced by cytokinins. A full-length promoter sequence of the isolated maize cytokinin oxidase gene, and functional fragments thereof, and variants thereof, and the use of such sequences with heterologous nucleotide sequences of interest, are described in the present invention. Unless otherwise specified, the notation "ckx1-2" in reference to the subject promoter includes SEQ ID NO: 1, SEQ ID NO: 4, and any functional fragments or variants thereof.

SUMMARY OF THE INVENTION

It is an object of the present invention to provide a novel nucleotide sequence for modulating gene expression in a plant.

It is a further object of the present invention to provide an isolated promoter capable of driving transcription in a tissue-preferred manner.

It is a further object of the present invention to provide an isolated promoter sequence responsive to the presence of cytokinin.

It is a further object of the present invention to provide a method of improved control of an endogenous or exogenous product in a transformed plant.

It is a further object of the present invention to provide a method for effecting useful changes in the phenotype of a transformed plant.

It is a further object of the present invention to provide a method for producing a novel product in a transformed plant.

It is a further object of the present invention to provide a method for producing a novel function in a transformed plant.

It is a further object of the present invention to provide a method for modulating the timing or rate of development of the seed of a transformed plant.

It is a further object of the present invention to provide a method for regulating the accumulation of photosynthetic products in the developing seed of a transformed plant.

It is a further object of the present invention to provide a method for regulating the production of phytohormones involved in seed development.

It is a further object of the present invention to provide a method for regulating the level of cytokinin oxidase activity within a plant.

It is a further object of the present invention to provide a method for regulating the cell cycle machinery of seeds during their development.

Therefore, in one aspect, the present invention relates to an isolated nucleic acid comprising a member selected from the group consisting of:

a) nucleic acids capable of driving expression in the carpel, pericarp, pedicel, glume, nucellus, endosperm, vascular tissue, or pedicel-forming region of a developing seed; in root tissue, especially vascular tissue; in stalk tissue; and in premeiotic anther tissue;

b) nucleic acids comprising a functional variant or fragment of at least 20 contiguous nucleotides of the sequence set forth in SEQ ID NO.: 4;

c) the nucleic acid sequence of SEQ ID NO.: 4; and d) nucleic acids that hybridize to any one of a), b), or c) under stringent conditions, wherein stringent conditions include hybridization at 42° C. in a solution of 50% (w/v) formamide, 6×SSC, 0.5% SDS, 100 ug/ml salmon sperm, washed with 0.5% SDS and 0.1×SSC at about 65° C. for 30 minutes and repeated.

In other aspects, the present invention relates to expression cassettes comprising the promoter operably linked to a nucleotide sequence, vectors containing said expression cassette, and plants stably transformed with at least one said expression cassette.

In a further aspect, the present invention relates to a method for modulating expression in the seed, root, stalk, or vascular tissue of a stably transformed plant comprising the steps of (a) transforming a plant cell with an expression cassette comprising the promoter of the present invention operably linked to at least one nucleotide sequence; (b) growing the plant cell under plant growing conditions and (c) regenerating a stably transformed plant from the plant cell wherein said linked nucleotide sequence is expressed in the seed, root, stalk, or vascular tissue.

Figure 1:
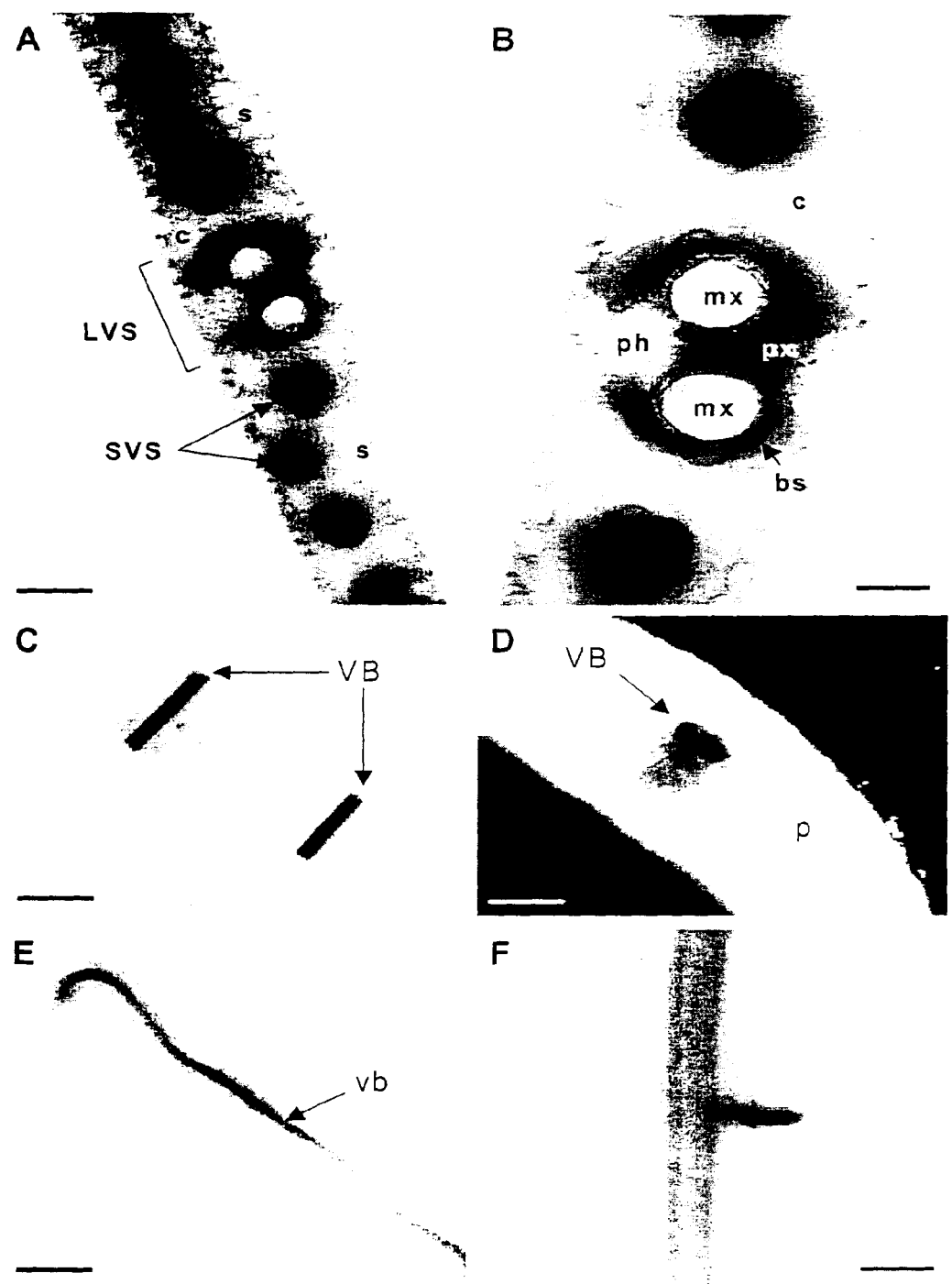
FIG. 1. Characterization of transgenic maize plants expressing a fusion of the ckx1-2 promoter (SEQ ID NO: 1) and the β-glucuronidase (GUS) gene.

(A) GUS staining of a leaf section showing strong labeling in a large vascular strand (LVS) and small vascular strands (SVS). Bar=250 μm.

(B) Close-up of a leaf section showing GUS staining in the protoxylem (px) and bundle sheath cells (bs) of a large vascular strand. Note the absence of staining in the phloem zone (ph). Bar=170 μm.

(C) GUS staining of a coleoptile cross-section showing strong labeling in the vascular bundles (VB). Bar=3 mm.

(D) Close-up of a transverse coleoptile section showing intense labeling in the vascular bundles. Bar=500 μm.

(E) Staining of lateral root showing GUS staining in the vascular bundle. Bar=250 μm.

(F) Staining of a primary root showing activity in emerging lateral root. Bar=250 μm.

s=stomata, c=cortex, mx=metaxylem, p=parenchyma

DETAILED DESCRIPTION OF THE INVENTION

In accordance with the invention, a nucleotide sequence is provided that favors initiation of transcription in specific tissues, including tissues of developing seed; roots, especially root vascular tissue; stalk tissue; and premeiotic anther tissue. The sequence of the invention comprises transcriptional initiation regions associated with said tissues. Thus, the compositions of the present invention comprise a novel nucleotide sequence for a plant promoter, more particularly a tissue-preferred promoter.

By "seed" or "kernel" is intended to include the grain or ripened ovule of a plant, or more broadly, a propagative plant structure. The terms "seed" and "kernel" are used interchangeably herein.

"Operably linked," as used herein, includes reference to a functional linkage between a promoter and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame. An endogenous promoter is operably linked to the endogenous coding region which it regulates.

As used herein, the term "plant" includes reference to whole plants and their progeny; plant cells; plant parts or organs, such as embryos, pollen, ovules, seeds, flowers, kernels, ears, cobs, leaves, husks, stalks, stems, roots, root tips, anthers, silk and the like. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plant are maize, canola, and soybean.

By "heterologous nucleotide sequence" is intended a sequence that is not naturally occurring with the promoter sequence. While this nucleotide sequence is heterologous to the promoter sequence, it may be homologous (native) or heterologous (foreign) to the plant host.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as the seed can be identified, isolated, and used with other core promoters to confirm seed-preferred expression. Promoter elements, such as those conferring cytokinin inducibility, may also be identified and isolated for use with other core promoters.

The isolated promoter sequence of the present invention can be modified to provide for a range of expression levels of the heterologous nucleotide sequence. Less than the entire promoter region can be utilized and the ability to drive tissue-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts. Generally, at least about 20 nucleotides of an isolated promoter sequence will be used to drive expression of a nucleotide sequence.

It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

By "tissue-preferred" promoter is meant a sequence which preferentially initiates transcription in certain tissues, such as leaves, roots, or seeds. A tissue-preferred promoter also may drive expression in certain tissues types in one or more organs; for example, in vascular tissues of roots or leaves.

By "seed-preferred" is intended favored expression in the seed, including at least one of embryo, seed or kernel, pericarp, endosperm, nucellus, aleurone, pedicel, and the like.

The term "isolated" refers to material, such as a nucleic acid or a protein, which is: (1) substantially or essentially free from components which normally accompany or interact with it as found in its natural environment. The isolated material optionally comprises material not found with the material in its natural environment; or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. The isolated nucleic acid may also be produced by the synthetic re-arrangement ("shuffling") of a part or parts of one or more allelic forms of the polynucleotide of interest. Likewise, a naturally-occurring nucleic acid (e.g., a promoter) becomes isolated if it is introduced to a different locus of the genome. Nucleic acids which are "isolated," as defined herein, are also referred to as "heterologous" nucleic acids.

Methods for isolation of promoter regions are well known in the art. See, for example, U.S. Pat. Nos. 6,797,859; 6,720,480; and 6,617,498, hereby incorporated by reference.

One sequence for the promoter region of the present invention is set forth in SEQ ID NO.: 4.

The promoter region of the invention may be isolated from any plant, including, but not limited to maize (*Zea mays*), canola (*Brassica napus*, *Brassica rapa* ssp.), alfalfa (*Medicago sativa*), rice (*Oryza sativa*), rye (*Secale cereale*), sorghum (*Sorghum bicolor*, *Sorghum vulgare*), sunflower (*Helianthus annuus*), wheat (*Triticum aestivum*), soybean (*Glycine max*), tobacco (*Nicotiana tabacum*), potato (*Solanum tuberosum*), peanut (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus* casica), guava (*Psidium guajava*), mango (*Mangifera indica*), olive (*Olea europaea*), oat (*Avena sativa*), vegetables, ornamentals, and conifers. Preferably, plants include maize, rice, soybean, sunflower, safflower, canola, wheat, rye, alfalfa, and sorghum.

Promoter sequences from other plants may be isolated according to well-known techniques based on their sequence homology to the promoter sequence set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see, e.g., Innis, et al., eds., (1990) *PCR Protocols, A Guide to Methods and Applications*, Academic Press).

Use of in situ hybridization preserves cellular morphology for subsequent interpretation and analysis. The following articles provide an overview of the various hybridization assay formats: Singer, et al., (1986) *Biotechniques* 4(3):230-250; Haase, et al., (1984) *Methods in Virology*, Vol. VII, pp. 189-226; Wilkinson, The theory and practice of in situ hybridization in: In situ Hybridization, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

The terms "stringent conditions" or "stringent hybridization conditions" include reference to conditions under which a probe will hybridize to its target sequence, to a detectably greater degree than to other sequences (e.g., at least 2-fold over background). Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 1000 nucleotides in length to about 250 nucleotides in length.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). See also, Sambrook et al. (1989) *Molecular Cloning: A Laboratory Manual* (2nd ed. Cold Spring Harbor Laboratory, Cold Spring Harbor, N.Y.).

In general, sequences that correspond to the promoter sequence of the present invention and hybridize to the promoter sequence disclosed herein will be at least 50% homologous, 70% homologous, and even 85% homologous or more with the disclosed sequence. That is, the sequence similarity between probe and target may range, sharing at least about 50%, 55%, 60%, 65%, 70%, 75%, 80%, and even about 85%, 86%, 87%, 88%, 89%, 90%, 91%, 92%, 93%, 94%, 95%, 96%, 97%, 98%, 99%, or 100% sequence similarity.

Specificity is typically the function of post-hybridization washes, the critical factors being the ionic strength and temperature of the final wash solution. Generally, stringent wash temperature conditions are selected to be about 5° C. to about 2° C. lower than the melting point ($T_m$) for the specific sequence at a defined ionic strength and pH. The melting point, or denaturation, of DNA occurs over a narrow temperature range and represents the disruption of the double helix into its complementary single strands. The process is described by the temperature of the midpoint of transition, $T_m$, which is also called the melting temperature. Formulas are available in the art for the determination of melting temperatures.

Preferred hybridization conditions for the promoter sequence of the invention include hybridization at 42° C. in 50% (w/v) formamide, 6×SSC, 0.5% (w/v) SDS, 100 µg/ml salmon sperm DNA. Exemplary low stringency washing conditions include hybridization at 42° C. in a solution of 2×SSC, 0.5% (w/v) SDS for 30 minutes and repeating. Exemplary moderate stringency conditions include a wash in 2×SSC, 0.5% (w/v) SDS at about 50° C. for 30 minutes and repeating. Exemplary high stringency conditions include a wash in 2×SSC, 0.5% (w/v) SDS, at about 65° C. for 30 minutes and repeating. Sequences that correspond to the promoter of the present invention may be obtained using all the above conditions. For purposes of defining the invention, the high stringency conditions are used.

Methods of alignment of sequences for comparison are well-known in the art. Optimal alignment of sequences for comparison may be conducted by the local homology algorithm of Smith and Waterman, (1981) *Adv. Appl. Math.* 2:482; by the homology alignment algorithm of Needleman and Wunsch, (1970) *J. Mol. Biol.* 48:443; by the search for similarity method of Pearson and Lipman, (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA. See, Higgins and Sharp, (1988) *Gene* 73:237-244; Higgins and Sharp, (1989) *CABIOS* 5:151-153; Corpet, et al., (1988) *Nucleic Acids Research* 16:10881-90; Huang, et al., (1992) *Computer Applications in the Biosciences* 8:155-65, and Pearson, et al., (1994) *Methods in Molecular Biology* 24:307-331.

Identity to the sequence of the present invention would mean a polynucleotide sequence having at least 80% sequence identity, more preferably at least 85% sequence identity, and most preferably at least 86%, 87%, 88%, 89%, 90%, 91%, 92%, 93%, 94%, 95%, 96%, 97%, 98%, 99% or 100% identity, wherein the percent sequence identity is based on the entire promoter region.

Fragments of a promoter nucleotide sequence disclosed herein are also encompassed by this invention. Such fragments will comprise at least about 20 contiguous nucleotides, preferably at least about 50 contiguous nucleotides, more preferably at least about 75 contiguous nucleotides, even more preferably at least about 100 contiguous nucleotides of the promoter nucleotide sequence disclosed herein. Such fragments will usually comprise the TATA recognition motif of the promoter sequence. Such fragments can be obtained by use of restriction enzymes to cleave the naturally-occurring promoter nucleotide sequences disclosed herein; by synthesizing a nucleotide sequence; through the use of PCR technology, and the like. See particularly, Mullis, et al. (1987) *Methods Enzymol.* 155:335-350, and Erlich, ed. (1989) *PCR Technology* (Stockton Press, New York).

Such fragments encompass, for example, sequences capable of driving tissue-preferred expression, elements responsible for temporal or tissue specificity, elements responsive to a phytohormone, and sequences useful as probes to identify similar sequences. Of particular interest are fragments which comprise one or more putative cis-elements, such as the as-1 like TGACG motif required for cytokinin response (Lam and Chua (1989) *The Plant Cell* 1:1147-1156; Benfey and Chua (1990) *Science* 250:959-966). Three putative as-1 like motifs are present in SEQ ID NO.: 4, at positions 958-962; 1334-1338; and 2408-2412.

Biologically active variants of the promoter sequence are also encompassed by the composition of the present invention, including variants resulting from site-directed mutagenesis. A regulatory "variant" is a modified form of a regulatory sequence wherein one or more bases have been modified, removed or added. For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digestion of a clone with this enzyme produces unidirectional nested deletions.

One example of a regulatory sequence variant is a promoter formed by one or more deletions from a larger promoter. The 5' portion of a promoter up to the TATA box near the transcription start site can be deleted without abolishing promoter activity, as described by Zhu, et al., (1995) *The Plant Cell* 7:1681-89. Such variants should retain promoter activity, particularly the ability to drive expression in specific tissues. Promoter activity can be measured by Northern blot analysis, reporter activity measurements when using transcriptional fusions, and the like. See, for example, Sambrook, et al., (1989) *Molecular Cloning: A Laboratory Manual* (2nd ed. Cold Spring Harbor Laboratory, Cold Spring Harbor, N.Y.), herein incorporated by reference.

The nucleotide sequence for the promoter of the invention, as well as fragments and variants thereof, can be provided in expression cassettes along with heterologous nucleotide sequences for expression in the plant of interest, more particularly in specific tissues of the plant. Such an expression cassette is provided with a plurality of restriction sites for insertion of the nucleotide sequence to be under the transcriptional regulation of the promoter. These expression cassettes are useful in the genetic manipulation of any plant to achieve a desired phenotypic response. This may be achieved by increasing expression of endogenous or exogenous products in the specific tissues of interest. Alternatively, there may be a reduction of expression of one or more endogenous products, particularly enzymes or cofactors.

General categories of genes of interest for the purposes of the present invention include, for example, those genes involved in information, such as Zinc fingers, those involved in communication, such as kinases, and those involved in housekeeping, such as heat shock proteins. Transgenes may include genes encoding important traits for agronomic quality, insect resistance, disease resistance, herbicide resistance, and grain characteristics. Other groups of transgenes may be used to effect expression of exogenous products such as enzymes, cofactors, and hormones from plants and other eukaryotes as well as from prokaryotic organisms. It is recognized that any gene of interest can be operably linked to the promoter of the invention and expressed in specific tissues.

Modifications that affect grain traits include alterations in the levels of saturated and unsaturated fatty acids. Likewise, increased levels of lysine- and sulfur-containing amino acids may be desired, as well as modifications of the amount and/or type of starch contained in the seed. Examples of hordothionin protein modifications are described in PCT publications WO94/16078 dated 21 Jul. 1994 and WO96/38563 dated 5 Dec. 1996; U.S. Pat. No. 5,885,801 issued Mar. 23, 1999, and U.S. Pat. No. 5,703,049 issued Dec. 30, 1997; the disclosures of which are incorporated herein by reference. Additional examples are lysine- and/or sulfur-rich seed protein encoded by the soybean 2S albumin described in PCT publication WO97/35023 dated 25 Sep. 1997, and the chymotrypsin inhibitor from barley, Williamson, et al., (1987) *Eur. J. Biochem.* 165:99-106, the disclosures of which are incorporated by reference.

Derivatives of the following genes can be made by site-directed mutagenesis to increase the level of preselected amino acids in the encoded polypeptide. For example, the gene encoding the barley high lysine polypeptide (BHL), is derived from barley chymotrypsin inhibitor, PCT publication WO98/20133 dated 14 May 1998. Other proteins include methionine-rich plant proteins such as from sunflower seed, Lilley, et al., (1989) *Proceedings of the World Congress on Vegetable Protein Utilization in Human Foods and Animal Feedstuffs*, Applewhite, H. (ed.); American Oil Chemists Soc., Champaign, IL:497-502; corn, Pedersen, et al., (1986) *J. Biol. Chem.* 261:6279; Kirihara, et al., (1988) *Gene* 71:359, both incorporated herein by reference; and rice, Musumura, et al., (1989) *Plant Mol. Biol.* 12:123. Other important genes encode latex, Floury 2, growth factors, seed storage factors and transcription factors.

Agronomic traits in seeds can be improved by altering expression of genes that affect seed growth and development during environmental stress, Cheikh-N, et al., (1994) *Plant Physiol.* 106(1):45-51, and genes controlling carbohydrate metabolism to reduce seed abortion in maize, Zinselmeier, et al., (1995) *Plant Physiol.* 107(2):385-391. In certain embodiments, the promoter of the instant invention modulates expression of genes encoding proteins which act as cell cycle regulators, or which affect carbohydrate metabolism or phytohormone levels, as has been shown in tobacco and canola with other tissue-preferred promoters. (Ma, et al., (1998) *Australian Journal of Plant Physiology* 25(1):53-59; Roeckel, et al., (1997) *Transgenic Research* 6(2):133-141.) Expression of heterologous nucleotides under the direction of the promoter may result in maintenance of a desirable phenotype that might otherwise be altered under adverse environmental conditions.

Insect resistance genes may encode resistance to pests that reduce yield, such as rootworm, cutworm, European corn borer, and the like. Such genes include, for example, *Bacillus thuringiensis* endotoxin genes, U.S. Pat. Nos. 5,366,892; 5,747,450; 5,737,514; 5,723,756; 5,593,881; Geiser, et al., (1986) *Gene* 48:109; lectins, Van Damme, et al., (1994) *Plant Mol. Biol.* 24:825; and the like.

Genes encoding disease resistance traits include detoxification genes, such as against fumonisin (PCT publication WO96/06175, dated 29 Feb. 1996); avirulence (avr) and disease resistance (R) genes (Jones, et al., (1994) *Science* 266: 789; Martin, et al., (1993) *Science* 262:1432; Mindrinos, et al., (1994) *Cell* 78:1089); and the like.

Alterations in gene expression may also affect the type or amount of products of commercial interest; for example, starch for the production of paper, textiles and ethanol. Another important commercial use of transformed plants is the production of polymers and bioplastics such as is described in U.S. Pat. No. 5,602,321 issued Feb. 11, 1997. Genes such as B-Ketothiolase, PHBase (polyhydroxybutyrate synthase) and acetoacetyl-CoA reductase (see, Schubert, et al., (1988) *J. Bacteriol* 170(12):5837-5847) facilitate expression of polyhyroxyalkanoates (PHAs).

The nucleotide sequence operably linked to the promoter disclosed herein can be an antisense sequence for a targeted gene. By "antisense sequence" is intended a nucleotide sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the promoter sequence disclosed herein can be operably linked to antisense DNA sequences to reduce or inhibit expression of a native protein in the plant.

The expression cassette may also include, at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., 1989) *Nucleic Acids Res.* 17:7891-7903; Joshi, et al., (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein, et al., (1989) *Proc. Nat. Acad. Sci. USA* 86:6126-6130; potyvirus leaders, for example, TEV leader (Tobacco Etch Virus), Allison, et al., (1986); MDMV leader (Maize Dwarf Mosaic Virus), *Virology* 154:9-20; human immunoglobulin heavy-chain binding protein (BiP), Macejak, et al., (1991) *Nature* 353:90-94; untranslated leader from the coat protein mRNA of alfalfa mosaic virus (AMV RNA 4), Jobling, et al., (1987) *Nature* 325:622-625); tobacco mosaic virus leader (TMV), Gallie, et al., (1989) *Molecular Biology of RNA*, pages 237-256; and maize chlorotic mottle virus leader (MCMV) Lommel, et al., (1991) *Virology* 81:382-385. See also, Della-Cioppa, et al., (1987) *Plant Physiology* 84:965-968. The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest under the control of the promoter. In general, the vectors should be functional in plant cells. At times, it may be preferable to have vectors that are functional in *E. Coli* (e.g., production of protein for raising antibodies, DNA sequence analysis, construction of inserts, obtaining quantities of nucleic acids). Vectors and procedures for cloning and expression in *E. Coli* are discussed in Sambrook, et al., (supra).

In certain embodiments the nucleic acid sequences of the present invention can be stacked with any combination of polynucleotide sequences of interest in order to create a plant with a desired phenotype with respect to one or more traits. For example, a hairpin construct of Example 6 may be "stacked" with a ckx1-2::csg construct such as is described in Example 5. The combinations generated may include multiple copies of any one or more of the polynucleotides of interest.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of a polynucleotide of interest. This may be combined with any combination of other suppression cassettes or overexpression cassettes to generate the desired combination of traits in the plant.

Vectors that are functional in plants can be binary plasmids derived from *Agrobacterium*. Such vectors are capable of transforming plant cells. These vectors contain left and right border sequences that are required for integration into the host (plant) chromosome. At a minimum, between these border sequences is the gene to be expressed under control of the promoter. In certain embodiments, a selectable marker and a reporter gene are also included. For ease of obtaining sufficient quantities of vector, a bacterial origin that allows replication in *E. coli* is preferred.

Reporter genes can be included in the transformation vectors. Examples of suitable reporter genes known in the art can be found in, for example, Jefferson, et al., (1991) in *Plant Molecular Biology Manual*, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *BioTechniques* 19:650-655; and Chiu, et al., (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella, et al., (1983) *EMBO J.* 2:987-992; methotrexate, Herrera Estrella, et al., (1983) *Nature* 303:209-213; Meijer, et al., (1991) *Plant Mol. Biol.* 16:807-820; hygromycin, Waldron, et al., (1985) *Plant Mol. Biol.* 5:103-108; Zhijian, et al., (1995) *Plant Science* 108:219-227; streptomycin, Jones, et al., (1987) *Mol. Gen. Genet.* 210:86-91; spectinomycin, Bretagne-Sagnard, et al., (1996) *Transgenic Res.* 5:131-137; bleomycin, Hille, et al., (1990) *Plant Mol. Biol.* 7:171-176; sulfonamide, Guerineau, et al., (1990) *Plant Mol. Biol.* 15:127-136; bromoxynil, Stalker, et al., (1988) *Science* 242:419-423; glyphosate, Shaw, et al., (1986) *Science* 233:478-481; phosphinothricin, DeBlock, et al., (1987) *EMBO J.* 6:2513-2518.

Other genes that could serve utility in the recovery of transgenic events but might not be required in the final product would include, but are not limited to, examples such as GUS (β-glucuronidase), Jefferson (1987) *Plant Mol. Biol. Rep.* 5:387); GFP (green florescence protein), Chalfie, et al., (1994) *Science* 263:802; luciferase, Teeri, et al., (1989) *EMBO J.* 8:343; and the maize genes encoding for anthocyanin production, Ludwig, et al., (1990) *Science* 247:449.

The transformation vector comprising the particular promoter sequence of the present invention, operably linked to a heterologous nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway, et al., (1986) *Biotechniques* 4:320-334; electroporation, Riggs, et al., (1986) *Proc. Natl. Acad. Sci. USA* 83:5602-5606; *Agrobacterium*-mediated transformation, see for example, Townsend, et al., U.S. Pat. No. 5,563,055; direct gene transfer, Paszkowski, et al., (1984) *EMBO J.* 3:2717-2722; and ballistic particle acceleration, see for example, Sanford, et al., U.S. Pat. No. 4,945,050; Tomes, et al., (1995) in *Plant Cell, Tissue, and Organ Culture: Fundamental Methods*, ed. Gamborg and Phillips (Springer-Verlag, Berlin); and McCabe, et al., (1988) *Biotechnology* 6:923-926. Also see, Weissinger, et al., (1988) *Annual Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); Klein, et al., (1988) *Plant Physiol.* 91:440-444 (maize); Fromm, et al., (1990) *Biotechnology* 8:833-839; Hooydaas-Van Slogteren, et al., (1984) *Nature* (London) 311:763-764; Bytebier, et al., (1987) *Proc. Natl. Acad. Sci. USA* 84:5345-5349 (Liliaceae); De Wet, et al., (1985) in *The Experimental Manipulation of Ovule Tissues*, ed. G. P. Chapman, et al., (Longman, New York), pp. 197-209 (pollen); Kaeppler, et al., (1990) *Plant Cell Reports* 9:415-418; and Kaeppler, et al., (1992) *Theor. Appl. Genet.* 84:560-566 (whisker-mediated transformation); D. Halluin, et al., (1992) *Plant Cell* 4:1495-1505 (electroporation); Li, et al., (1993) *Plant Cell Reports* 12:250-255 and Christou, et al., (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

The cells that have been transformed can be grown into plants in accordance with conventional ways. See, for example, McCormick, et al., (1986) *Plant Cell Reports* 5:81-84. These plants can then be grown, and pollinated with the same transformed strain or different strains. The resulting plant having appropriate expression of the desired phenotypic characteristic can then be identified. Two or more generations can be grown to ensure that the desired phenotype is stably maintained and inherited.

All publications and patent applications mentioned in the specification are indicative of the level of those skilled in the art to which this invention pertains. All publications and patent applications herein are hereby incorporated by reference to the same extent as if each individual publication or patent application was specifically and individually indicated to be incorporated by reference.

The following examples are offered by way of illustration and not by way of limitation.

EXAMPLE 1

In Situ Localization of Cytokinin Oxidase mRNA in Selected Maize Tissues

To determine expression patterns of cytokinin oxidase (cytox) in maize, in situ hybridization was performed using the protocol of Jackson, (1991) (In situ Hybridization in Plants, *Molecular Plant Pathology: A Practical Approach*, D. J. Bowles, S. J. Gurr, and M. McPherson, eds. Oxford University Press, England, pp. 63-74). Sense and antisense mRNA probes of about 1 kb corresponding to cytox cDNA were labeled non-isotopically with digoxigenin and incubated with fixed sections of maize tissues from immature ear (7 weeks after planting), kernel at silking (9 weeks after planting), kernels at 8 and 12 days after pollination (DAP), primary root tip at the V6 stage, and premeiotic anthers. Following extensive washing to remove unbound probe, sections were incubated with alkaline phosphatase-conjugated anti-digoxigenin antibody to detect areas of probe hybridization. Cytox mRNA was detected specifically with the antisense probe; the sense probe did not hybridize, therefore serving as a negative control.

In immature ears, there is low-level expression throughout the ear tissue and developing flower. Expression is slightly elevated in the tissue subtending the flower (pedicel region), in vascular bundles of the ear and silk, megaspore mother cell (developing embryo sac) and rudimentary anthers.

Two weeks later, at the time of silking, expression is still low in the developing ovule (nucellus and upper carpel walls), but is strongly elevated in pedicel and part of the vascular bundles in the pedicel, as well as in glumes.

In kernels at 8 DAP, cytox is strongly expressed in the pericarp, nucellus, pedicel, and endosperm (except the basal endosperm transfer region). It is weak or absent in the embryo and placental-chalazal region. Some regions of the pedicel show lower levels of expression, whereas the vascular strands show a strong signal. Analysis of transverse sections probed with cytox reveal that the cells of the vascular bundles that show strong signal are protoxylem and protophloem elements. Metaxylem and metaphloem (the more mature elements) show no signal.

In 12 DAP kernels, strong cytox expression is observed in the pedicel (especially vascular bundles) and intermediate expression in pericarp and endosperm. Expression is low in embryo, basal part of endosperm and placental-chalazal region.

In primary roots, strong cytox expression is seen in all tissues of the cell elongation zone, starting about 6 mm above the root tip. Signal is strong in vascular bundles, even in those that extend into the region of lower signal towards the root tip. Signal is low or absent in root meristem and root cap, except for the outermost layer (epidermis).

In premeiotic anthers, a strong signal is observed in the glumes and the outer layers of the anther wall. The signal is weaker in tapetum and microspores.

EXAMPLE 2

Generation of Transgenic Events Via *Agrobacterium* Transformation

The *Agrobacterium* strain utilized in this example was modified to contain nucleic acid encoding the cytokinin oxidase promoter and a GUS reporter gene to be expressed in the transformed cells.

The vectors of this example were constructed using standard molecular biology techniques known to those of ordinary skill in the art. A reporter gene and a selectable marker gene were inserted between the T-DNA borders of a superbinary vector. The reporter gene was the b-glucuronidase (GUS) gene (Jefferson, et al., (1986) *Proc. Natl. Acad. Sci. (USA)* 83:8447-8451) into whose coding region was inserted the second intron from the potato ST-LS1 gene (Vancanneyt, et al., (1990) *Mol. Gen. Genet.* 220:245-250), to produce intron-GUS, in order to prevent expression of the gene in *Agrobacterium* (see, Ohta, et al., (1990) *Plant Cell Physiol.* 31(6):805-813). A fragment containing bases 2 to 310 from the terminator of the potato proteinase inhibitor (pinII) gene (An, et al., (1989) *Plant Cell* 1:115-122) was blunt-end ligated downstream of the GUS coding sequence, to create the GUS expression cassette.

For the selectable marker, a Cauliflower Mosaic Virus 35S promoter with a duplicated enhancer region (2×35S; bases −421 to −90 and −421 to +2 from Gardner, et al., (1981) *Nucl. Acids Res.* 9:2871-2888) was created. A fragment containing the first intron of the maize alcohol dehydrogenase gene ADH1-S (Dennis, et al., (1984) *Nucl. Acids Res.* 12:3983-3990) was inserted downstream of the 35S promoter. The BAR coding sequence (Thompson, et al., (1987) *EMBO J.* 6:2519-2523) was cloned downstream of the leader sequence, with the pinII terminator ligated downstream of BAR, to create the BAR expression cassette.

In summary, the plasmid was constructed by inserting the GUS expression cassette and the BAR expression cassette between the right and left T-DNA borders in pSB11. The GUS cassette was inserted proximal to the right T-DNA border. The ckx1-2 promoter fragment (SEQ ID NO: 1) was inserted into the vector in front of the intron-GUS gene. The plasmid pSB11 was obtained from Japan Tobacco Inc. (Tokyo, Japan). The construction of pSB11 from pSB21 and the construction of pSB21 from starting vectors has been described by Komari, et al., (1996, *Plant J.* 10:165-174). The T-DNA of this plasmid was integrated into the superbinary plasmid pSB1 (Saito, et al., EP 672 752 A1) by homologous recombination between the two plasmids. The plasmid pSB1 was also obtained from Japan Tobacco Inc. *E. coli* strain HB101 containing the plasmid containing the ckx1-2 promoter (SEQ ID NO: 1) was mated with *Agrobacterium* strain LBA4404 harboring pSB1 to create the cointegrate plasmid in the *Agrobacterium tumefaciens* strain LBA4404 using the method of Ditta, et al., (*Proc. Natl. Acad. Sci. USA* 77:7347-7351, 1980). (See also, U.S. Pat. No. 5,981,840 for a further discussion of *Agrobacterium*-mediated transformation.)

The resulting co-integrated plasmid, the product from the tri-parental mating described above, was transformed into the genotypes (1) Hi-II and (2) Hi-II×PHN46. (See, U.S. Pat. No. 5,567,861 for more information about PHN46.) TO plants were generated and promoter analysis was conducted on T1 seed from both genotypes.

EXAMPLE 3

Expression of a Cytokinin Oxidase Promoter-GUS Fusion Construct in Transgenic Maize The ckx1-2 promoter of SEQ ID NO: 1 was isolated using the Genome Walker™ cloning kit with genomic DNA from the inbred B73. The procedure for promoter isolation is described in the User Manual for the Genome Walker™ cloning kit sold by Clontech Laboratories, Inc., Palo Alto, Calif. (Genome Walker™ User Manual Clontech PT3042-1 version PR68687)

The promoter was fused to GUS. Maize embryos were transformed with the ckx1-2 (SEQ ID NO: 1): GUS construct via *Agrobacterium*. After regeneration, leaf discs of 8-week old TO plants were assayed for GUS activity. GUS staining was detected in three independent transgenic events and the event showing the strongest signal was used for further analysis. Strong GUS staining was found in the leaf midrib and in small and large vascular strands (FIG. 1A). In the large vascular strands, label was confined to protoxylem and bundle sheath cells (FIG. 1B). No or little staining was observed in phloem tissue, epidermis or cortex. As shown in FIGS. 1C and D, vascular staining was also observed in coleoptile sections of T1 seedlings. In secondary roots of the same seedlings, staining was primarily found in the vasculature (FIG. 1E). Staining was stronger in the root elongation zone and decreased in the upper region of the root. Weak or no staining was detected in the vasculature of primary roots but occasional pigmentation was detected in developing root primordia (FIG. 1F). The ckx1-2 promoter (SEQ ID NO: 1) was also found to be active in the base of tassel spikelets, pedicels of 8 DAP kernels, and in the vasculature of tassel spikelet glumes (data not shown).

Based on the analysis of ckx1-2 (SEQ ID NO.: 1): GUS transgenic plants, several constructs were generated for transformation into maize. These constructs contained the ckx1-2 promoter fused to polynucleotides that encode proteins involved in the synthesis of cytokinins and the stimulation of the cell cycle.

EXAMPLE 4

Isolation of Additional 5' Sequence

A maize bacterial artificial chromosome (BAC) library derived from inbred Mo17 was screened using a probe representing the ckx1-2 promoter sequence previously identified (see SEQ ID NO: 1). The Qiagen® Large-Construct Kit (Qiagen, Inc., 27220 Turnberry Lane, Valencia, Calif. 91355) was used according to the manufacurer's instructions to isolate BAC DNA from positive clones. Using the GenomeWalker™ cloning kit (Clontech Laboratories, Inc., Palo Alto, Calif.) according to the manufacturer's instructions, and appropriate sequence-specific primers (see, SEQ ID NO: 5-9), 3.3. kb of sequence 5' to the ckx1-2 coding sequence was amplified and sequenced (SEQ ID NO: 4).

EXAMPLE 5

Use of Cytokinin Oxidase Promoter in Regulating Cytokinin Biosynthesis

An example of one predicted phenotype of a transgenic event containing a ckx1-2::csg (cytokinin synthesis gene) construct is described here. External application of cytokinins has previously been shown to stimulate cytokinin oxidase activity in plants. Using a leaf disc assay and in vitro kernel culture, it has been demonstrated that this induction occurs at the transcript level, which likely means that cytokinin application causes an increase in cytokinin oxidase promoter activity. Research also showed, in vivo, that in developing kernels, cytokinin oxidase transcripts accumulate in response to an increase in cytokinin levels. It has been demonstrated in numerous experiments that application of cytokinins enhances sink strength. In addition, there is experimental evidence which indicates that abiotic stress (in particular heat stress) causes an elevation in cytokinin oxidase message in developing kernels. Thus, it is predicted that under normal environmental conditions or transient abiotic stress conditions, cytokinin levels in sink tissues (such as developing kernels) of ckx1-2::csg events would maintain sink activity (cell division, amyloplast differentiation, etc.) with either an enhanced or stabilized grain yield. The interest in using this promoter also derives from the fact that, since it reacts to cytokinin in vivo, it most likely directs expression in or around the tissue where natural cytokinin biosynthesis occurs in plants. Based on work in Urtica dioica, Pisum sativum and maize, it has been shown that cytokinins are translocated in the plant via the xylem. Interestingly, a mutant in a cytokinin receptor-kinase (Cre1) has been shown to display abnormal vascular differentiation in Arabidopsis. Thus, one would predict that maize events containing a ckx1-2::csg construct would also produce more cytokinins in leaf and root vasculature. This synthesis of cytokinins would stimulate the ckx1-2 promoter, which in turn would initiate more cytokinin production. In summary, the overall elevation in cytokinins in the plant would both increase the sink strength of a particular organ (such as the kernel) and enhance overall growth of the plant by stimulating vascular cell division and/or differentiation.

EXAMPLE 6

Downregulation of Cytokinin Catabolism

The ckx1-2 promoter of the present invention can be used in constructs designed to downregulate cytokinin oxidase. For example, certain embodiments comprise a construct comprising a segment of the ckx1-2 promoter such that, upon expression, self-hybridization of the RNA results in formation of hairpin RNA (hpRNA), resulting in transcriptional gene silencing of the native cytokinin oxidase gene. That is, the embodiment comprises a nucleotide sequence which, when expressed in a cell, forms a hairpin RNA molecule (hpRNA), which suppresses (i.e., reduces or eliminates) expression of the endogenous cytokinin oxidase gene from its endogenous promoter. The ability of hpRNAs to suppress expression of a gene has been described (see, e.g., Matzke, et al., (2001) Curr. Opin. Genet. Devel. 11:221-227; Scheid, et al., (2002) Proc. Natl. Acad. Sci., USA 99:13659-13662; Waterhouse and Helliwell (2003) Nature Reviews Genetics 4:29-38; Aufsaftz, et al., (2002) Proc. Nat'l. Acad. Sci. 99(4): 16499-16506; Sijen, et al., (2001) Curr. Biol 11:436-440).

The promoter which is operably linked to the nucleotide sequence encoding the hpRNA can be any promoter that is active in plant cells, particularly a promoter that is active (or can be activated) in reproductive tissues of a plant. As such, the promoter can be, for example, a constitutively active promoter, an inducible promoter, a tissue-specific promoter, a tissue-preferred promoter, a developmental stage specific promoter, or a developmental stage preferred promoter.

A hairpin may target a single promoter or may target two or more promoters by means of a single transcribed RNA. The hairpin-encoding region may be located in any appropriate position within the construct, such as within an intron of an encoded gene or within 5' or 3' non-coding regions, or may be the sole expressed element of the construct.

Methods for preparing said constructs and transforming plants may be as previously described (for example, see, Cigan, et al., (2001) Sex Plant Reprod. 14:135-142).

Said constructs for downregulating cytokinin oxidase expression may be used in combination with constructs or methods to increase cytokinin biosynthesis activity, such as those described in Example 5.

That which is claimed is:

1. A construct comprising a first nucleotide sequence which shares sufficient sequence identity with SEQ ID NO: 4 the ckx1-2 promoter of that, when expressed, a hairpin RNA molecule is formed which suppresses expression of a second nucleotide sequence operably linked to the ckx1-2 promoter.

2. A method of suppressing cytokinin oxidase activity in a plant, comprising transformation of a plant host cell with the genetic construct of claim 1 and regenerating and recovering from said transformed cell a transgenic plant wherein expression of the endogenous cytokinin oxidase gene is reduced or eliminated.

* * * * *

UNITED STATES PATENT AND TRADEMARK OFFICE
CERTIFICATE OF CORRECTION

PATENT NO.      : 7,741,534 B2
APPLICATION NO. : 12/051893
DATED           : June 22, 2010
INVENTOR(S)     : Xiaomu Niu et al.

It is certified that error appears in the above-identified patent and that said Letters Patent is hereby corrected as shown below:

Col. 25 line 19-20

In Claim 1, the phrase "the ckx1-2 promoter of" should be moved to a position directly prior to "SEQ ID NO: 4". The claim will then read as follows:

1. A construct comprising a first nucleotide sequence which shares sufficient sequence identity with the ckx1-2 promoter of SEQ ID NO: 4 that, when expressed, a hairpin RNA molecule is formed which suppresses expression of a second nucleotide sequence operably linked to the ckx1-2 promoter.

Signed and Sealed this
Fifteenth Day of February, 2011

David J. Kappos
*Director of the United States Patent and Trademark Office*

SEQUENCE LISTING

<160> NUMBER OF SEQ ID NOS: 9

<210> SEQ ID NO 1
<211> LENGTH: 1470
<212> TYPE: DNA
<213> ORGANISM: Zea mays

<400> SEQUENCE: 1

```
gagctcgccc ttgcatgctt gagtcatatc ttggaaaaaa aaactgtaac ttaaagtatg      60
atctatatat ggattatttg gatgggatgt cattttcgta tcaccaacca aaattacagt     120
ttggtcgtgc gtagaaattc tacctactag ctgaaacaac ggctgctatg tataactact     180
ggtactggaa agaatattag tcattgactc aaaattagaa tgcatgtgta agtcatgcgt     240
```

```
gctaatttgt tctatcagca ttcggcgaat tccgaagtcc gtacgtgttg ttcgtggagg      300
agaggaaaac atcagaaatg acaaaactag acggcgtgtg cttctacact gaattcatca      360
acatttgttt tacttttact agagaatggc atcagatgga aaaccgctga aaaaacaaga      420
aaacaattgg accccaaata tgtacagacg ctagctatag ccagccacac tgaagttgac      480
atgcggcaac tagctaacca ccttctctga aacactaaca tttgtacctt ggtcgtgtaa      540
gtgtagttag taacgtatgt tgacgcgact taccgaacaa aaatataatt gtcccaatca      600
agctagggac gattgtttgt ttccaaaatg ttgccatttg cttaatcaat cctatattga      660
ttcatggctg ttaaggtgag ataaagcgac aagaaatctc tctctatata tatatataag      720
atcccgaagg ctagcgacat ttttgatagc aaaatatgag aagttggcag gttctggtag      780
caaatcaaat aatatggcca gaataatcgt ggctagcttg attaaacctt cagcttggtg      840
tattttggaa gtcgaccaac cagctgggcc ggggctcgtc gtagtaccaa aattacagcc      900
tgcttccttc gtcgtcctgt acgtaatgca gtacagctgt ctgtctagta gagacgattt      960
tgagcaggca cacacattaa gtgataacat aaaagacggc ttcattttat ttcataacca     1020
aacgatatgg tcaacacaca cctatagcta ccaaatttgt acaactattt agtgcgaaaa     1080
ctatttcatt ctcaagaatt gatcgcttat atttattatt acaggttttt aaatgtataa     1140
atacgctata ttgcatggca aaggggggta ataattaggc aggactatat atataatagt     1200 ttttttttcct ttaaattctt gggaggatgg taaagttggt aactaggcac cttgtgcgca     1260 tattttctg tggtcaaaca gaataaaact agacgggatg cagaattttt ttttccttgg     1320
aaagcagctc atctctgtgt tcgagtacgt aattgaagaa gtatgtgatc gcactacacc     1380
tacacgtatg tgccgccgta tccgtcctat atatatacgg ggtgcaatca cctagttacc     1440
aaacactcac acataagggc ggatccatgg                                      1470

<210> SEQ ID NO 2
<211> LENGTH: 25
<212> TYPE: DNA
<213> ORGANISM: Zea mays

<400> SEQUENCE: 2
gcatgcttga gtcatatctt ggaaa                                            25

<210> SEQ ID NO 3
<211> LENGTH: 27
<212> TYPE: DNA
<213> ORGANISM: Zea mays

<400> SEQUENCE: 3
atgtgtgagt gtttggtaac taggtga                                          27

<210> SEQ ID NO 4
<211> LENGTH: 3317
<212> TYPE: DNA
<213> ORGANISM: Zea mays
<220> FEATURE:
<221> NAME/KEY: misc_signal
<222> LOCATION: (958)...(962)
<223> OTHER INFORMATION: as-1 like TGACG motif
<221> NAME/KEY: misc_signal
<222> LOCATION: (1334)...(1338)
<223> OTHER INFORMATION: as-1 like TGACG motif
<221> NAME/KEY: misc_signal
<222> LOCATION: (2408)...(2412)
<223> OTHER INFORMATION: as-1 like TGACG motif

<400> SEQUENCE: 4
```

-continued

```
tcttgttccc aagtgttttg taagcaaggc aagagacacc aagtgtgtgg tggtccttgc        60
ggggtctaag tgacccattt gattaaggag aaggctcact cggtctaagt gaccgtttga       120
gagagtgaaa gggttgaaag agacccggtc tttgtgacca cctcaatggg gactaggttc       180
tttagaaccg aacctcggta aaagaaatca tcgtgttcat ccgctttatt tcttggttga       240
tttgttttc ccctctctcc cgaactcgga tttaattcta acgctaaccc cggcttgtag        300
tttatgtttt aagttgtaaa tttcagatta cgcctattca cccccctaggc aactttcagt     360
tccaccactc ctccccacct tgtacttacg aaagattgtg ttagtagatc tcgagattta      420
caaacttacc ataagcaact aaaaataata taaacctaaa aatatgaaaa cccggaaaga      480
gcctaaaact tgaacccgga aaaaaattcc tgcaataatc ataatcaact aagttatgct      540
cacacattag gtctgcgttg ttgaattaac tttcaagacc agaaaacagg cacgcgtgca     600
tcgtacaagt ggaacttcca aacctttaag taaatagaga tagacacgcc cacatgtgga      660
acttcttggt acgtaatgcg tgacaagtta gaagtgaaca aggcaaccac gtcgctactt       720
gtgatgaata ctgggctgtg tgtgggtttt gtcgtcgcag gagtacatgt gttctctgaa       780
ttctaaatcg atcatgatgt ccgtcttttt tttattttag ccctttttta gttttttttc      840
ataaatatgc cctttctagt tttaactcaa aaaatggacc ctctggtcga caccattact      900
attggcggca acctaacacg tctaggcgcc tagacggcta gaccttgttc gtggcattga      960
cgtggtgcac ccgtggctag tgaggtggca gaggtaggcg ctaagaacta tagtgccgaa     1020
ggtaggcggc atatatcttg gcacaggccc cctttaatac gggcccacgt gtaatttat     1080
tttcctttc ctcactctcc accctcgtcg ttcgcctggc tcaacatagc cgcccctctc      1140
cctctccgcg tctcgccatc gtcgcccctc tcctcgcagt gacttgccat ggtcgcggct     1200
caccgtggcc acgccatgcc agcgtcagcc cgctccctca tttatcgatg cgggctcggt     1260
ggtcggcgac gagcgcaagg ctgaggagcg tgggcgggcg acgtggtga gcgacgtagg      1320
acgccgacga cggtgacggg cgacttaggg caccgacgac gtatggcgtg ggcgggcgcc     1380
agcggcctca ccgacggagg atggcgcggg caacgctgga gagtggccga gcagcgaccg     1440
ggtcgaatgg aagagagaga aagaggaaaa gaacgtgaac cgattggtat atagagggtc     1500
ggcgctaaga tctatggcgt cgatccatac catgcctcag ggtccttcct ggccacgtca     1560
tcgatacata tgcgtcaatt gcattggcac caatacgtgt taggttggca ccaatagtga     1620
gagcgtcaac ctaagggtcc atattctgaa ttcaaacaaa aaataaccta tttgtgaaaa     1680
tgaaacacta aaaaggctaa aatagaaaaa aaatcggtcg cgatgcagac gcatcgtcgg     1740
tttcaccgcc gtcacgcgcg cgtctgtatg cgctgccagg agtcactgca agcggcaagc     1800
agccaaaaaa ataaaaattg gctgcatccg atctcgagac tccgacgaga ggaggctgcg     1860
catgcttgag tcatatcttg gaaaaaaaaa ctgtaactta agtatgatc tatatatgga      1920
ttatttggat gggatgtcat tttcgtatca ccaaccaaaa ttacagtttg gtcgtgcgta     1980
gaaattctac ctactagctg aaacaacggc tgctatgtat aactactggt actggaaaga    2040
atattagtca ttgactcaaa attagaatgc atgtgtaagt catgcgtgct aatttgttct    2100
atcagcattc ggcgaattcc gaagtccgta cgtgttgttc gtggaggaga ggaaaacatc    2160
agaaatgaca aaactagacg gcgtgtgctt ctacactgaa ttcatcaaca tttgttttac    2220
ttttactaga gaatggcatc agatggaaaa ccgctgaaaa aacaagaaaa caattggacc    2280
ccaaatatgt acagacgcta gctatagcca gccacactga agttgacatg cggcaactag    2340
```

-continued

```
ctaaccacct tctctgaaac actaacattt gtaccttggt cgtgtaagtg tagttagtaa    2400
cgtatgttga cgcgacttac cgaacaaaaa tataattgtc ccaatcaagc tagggacgat    2460
tgtttgtttc caaatgttg ccatttgctt aatcaatcct atattgattc atggctgtta     2520
aggtgagata aagcgacaag aaatctctct ctatatatat atataagatc ccgaaggcta    2580
gcgacatttt tgatagcaaa atatgagaag ttggcaggtt ctggtagcaa atcaaataat    2640
atggccagaa taatcgtggc tagcttgatt aaaccttcag cttggtgtat tttggaagtc    2700
gaccaaccag ctgggccggg gctcgtcgta gtaccaaaat tacagcctgc ttccttcgtc    2760
gtcctgtacg taatgcagta cagctgtctg tctagtagag acgattttga gcaggcacac    2820
acattaagtg ataacataaa agacggcttc attttatttc ataaccaaac gatatggtca    2880
acacacacct atagctacca aatttgtaca actatttagt gcgaaaacta tttcattctc    2940
aagaattgat cgcttatatt tattattaca ggttttaaa tgtataaata cgctatattg     3000
catggcaaaa gggggtaata attaggcagg actatatata taatagtttt ttttcctta    3060 aattcttggg aggatggtaa agttggtaac taggcacctt gtgcgcatat ttttctgtgg    3120
tcaaacagaa taaaactaga cgggatgcag aattttttt tccttggaaa gcagctcatc    3180
tctgtgttcg agtacgtaat tgaagaagta tgtgatcgca ctacacctac acgtatgtgc    3240
cgccgtatcc gtcctatata tatacgggt gcaatcacct agttaccaaa cactcacaca     3300
taagggcgga tccatgg                                                    3317
```

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
gccgttgttt cagctagtag g                                                21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ctctctcttc cattcgaccc g                                                21

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
atacgtcgtc ggtgccctaa gtcg                                             24

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8

-continued

```
taatggtgtc gaccagaggg                                              20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
aagacggaca tcatgatcga                                              20
```